US009867965B1

(12) United States Patent  
Kantor et al.

(10) Patent No.: US 9,867,965 B1  
(45) Date of Patent: Jan. 16, 2018

(54) MEDICAL BANDAGE FOR THE HEAD, A LIMB OR A STUMP

(71) Applicants: Deborah Kantor, Ponte Verda Beach, FL (US); Sherrin Whiteman, Jacksonville Beach, FL (US)

(72) Inventors: Deborah Kantor, Ponte Verda Beach, FL (US); Sherrin Whiteman, Jacksonville Beach, FL (US)

(73) Assignee: BYO HEALTH, L.L.C., Jacksonville Beach, FL (US)

( * ) Notice: Subject to any disclaimer, the term of this patent is extended or adjusted under 35 U.S.C. 154(b) by 259 days.

(21) Appl. No.: 14/694,497

(22) Filed: Apr. 23, 2015

Related U.S. Application Data

(60) Provisional application No. 61/984,324, filed on Apr. 25, 2014.

(51) Int. Cl.  
*A61F 13/12* (2006.01)  
*A61M 25/02* (2006.01)  
(Continued)

(52) U.S. Cl.  
CPC .......... *A61M 25/02* (2013.01); *A61B 17/0218* (2013.01); *A61F 13/00029* (2013.01); *A61F 13/06* (2013.01); *A61F 13/10* (2013.01); *A61F 13/12* (2013.01); *A61F 13/45* (2013.01); *A61M 5/44* (2013.01); *A61B 2017/0225* (2013.01); *A61F 2007/0002* (2013.01); *A61F 2007/0008* (2013.01); *A61F 2007/0029* (2013.01); *A61F 2007/0039* (2013.01); (Continued)

(58) Field of Classification Search  
CPC .......... A61F 13/06; A61F 13/10; A61F 13/12; A61F 13/00029; A61F 2007/0002; A61F 2007/0008; A61F 2007/0029; A61F 2007/0039; A61F 2007/0051; A61F 7/03  
USPC .............................................. 602/60, 61, 74  
See application file for complete search history.

(56) References Cited

U.S. PATENT DOCUMENTS 3,464,413 A 9/1969 Goldfarb et al.  
3,600,717 A 8/1971 Mckeehan  
(Continued)

OTHER PUBLICATIONS www_gvequine_com-Pages-ht_SOAK_AND_WRAP_A_HOOF_php How to Soak and Wrap a Hoof Published by; Genesee Valley Equine Clinic LLC 2012 Dicovered Dec. 12, 2012.

*Primary Examiner* — Keri J Nelson  
(74) *Attorney, Agent, or Firm* — H. John Rizvi; Gold & Rizvi, P.A.

(57) ABSTRACT

A medical bandage is provided, capable of being rapidly, adjustably, intuitively and universally fitted on a head, limb or stump, for instance to conceal and protect a wound. The medical bandage is cap-shaped, and is formed of several layers, and comprised at least one port for obtaining quick access to a wound concealed by the medical bandage. When open, a port can stabilize a drainage tube, or provide a passage through which to easily and rapidly apply a medicine. The medical bandage can be directly fit on the head or other body part, providing an all-in-one dressing, wrap and treatment, and eliminating the need for cumbersome and difficult to manage gauze roll and multiple bandages of various sizes, shapes, and uses. The medical bandage provides simple, rapid, and effective treatment of emergency trauma wounds, and improved medical treatment of acute or chronic wounds.

19 Claims, 8 Drawing Sheets

(51) Int. Cl.
*A61M 5/44* (2006.01)
*A61B 17/02* (2006.01)
*A61F 13/45* (2006.01)
*A61F 13/10* (2006.01)
*A61F 13/00* (2006.01)
*A61F 13/06* (2006.01)
*A61F 7/00* (2006.01)

(52) U.S. Cl.
CPC ......... *A61F 2007/0051* (2013.01); *A61F 2013/4506* (2013.01); *A61M 2025/0206* (2013.01)

(56) References Cited

U.S. PATENT DOCUMENTS

| | | | |
|---|---|---|---|
| 5,031,609 A | | 7/1991 | Fye |
| 5,785,980 A | * | 7/1998 | Mathewson ......... A41D 20/005 424/402 |
| 5,916,190 A | | 6/1999 | Davis |
| 7,296,570 B2 | * | 11/2007 | Hutchinson ............... A61F 7/02 128/201.26 |
| 7,575,561 B2 | | 8/2009 | Smith et al. |
| 8,262,601 B2 | | 9/2012 | Cumming et al. |
| 8,481,804 B2 | | 7/2013 | Timothy |
| 2006/0163101 A1 | | 7/2006 | Assie et al. |
| 2012/0296252 A1 | * | 11/2012 | Cumming ............... A61F 13/12 602/45 |
| 2014/0288476 A1 | * | 9/2014 | Wright ................... A61F 13/12 602/48 |

* cited by examiner

MEDICAL BANDAGE FOR THE HEAD, A LIMB OR A STUMP

CROSS-REFERENCE TO RELATED APPLICATION

This application claims the benefit of U.S. Provisional Patent Application Ser. No. 61/984,324, filed on Apr. 25, 2014, which is incorporated herein in its entirety.

FIELD OF THE INVENTION

The present invention relates generally to a medical bandage and, in particular, to a cap-shaped medical dressing or bandage conveniently shaped to cover a wound on a patient's head, limb, or stump, for emergency, post-surgical, or chronic wound care, for instance in the event of a bleeding cranial wound or in the event or curing an amputated limb. The present invention provides access ports to the wound in order to support or stabilize wound drains, or apply medicine to the wound.

BACKGROUND OF THE INVENTION

Typically, a medical bandage or dressing is a covering or wrap that protectively conceals a wounded area of the body in order to stem the flow of body fluids from the wound, absorb body fluids from the wound, ease pain, debride the wound, protect the wound from infection, promote healing of the wound, and/or reduce psychological stress. Medical bandages are used for many different healthcare situations such as for emergency, post-surgical, or chronic care of a wound. Normally, bandages or dressings are in direct contact with the wound, and are covered with an adhesive film to hold them in place. Dressings can be marketed in various configurations; in a first example, dressings are sold alone in rolls, sheets or pads, to be directly applied on or around a body portion; in another example, a dressing and a corresponding adhesive band are sold as an integral product. Generally, dressings are sold in a flat configuration, to cover a substantially flat surface of the body. In the event that a curved surface is to be covered, the dressing is deformed to adopt the shape of the surface. Similarly, in the event that a full perimetric surface must be covered, such as a wrist or knee, the dressing is deformed to wrap around the perimetric surface.

It is well known that traumatic amputations are generally gruesome, devastating injuries that may result in death. Similarly, head injuries often result in trauma to the scalp, skull, or brain. These injuries frequently result in extreme blood loss which can contribute greatly to the associated fatality rate. The time required to control the bleeding of an amputation is vital in reducing blood loss. Often, quickly covering the wounds on the amputated limb or head helps to stop further blood loss during emergency care, and maintaining a suitable bandage can help protect the wound, promote wound healing and prevent infection. However, the dressing and bandage materials known in the art are often cumbersome to handle and difficult to appropriately deform and apply, particularly on an immobilized victim. Due to different settings, injuries, and access to care, medical professionals must use a multitude of sizes, shapes, styles of bandages for covering and treating wounds of the head or limb. In consequence, it is not rare that medical professionals are required to heavily manipulate dressings in order to fit them onto the head or onto a stump, leading to a great loss of time and to an increased risk of the dressings being contaminated or placed ineffectively from such manipulation. A person skilled in the art will clearly understand that the more ready, intuitive, and universally applied the medical devices and instruments are, the more effective and successful the treatment can be for immediate medical and post-traumatic wound care. In addition, promoting wound healing of the head or a limb can be a lengthy process requiring days to months of dressing changes and wound care. Having to repeatedly and manually wind and unwind conventional dressings (not particularly indicated for the head or limb) over the head or limb is cumbersome and extremely labor consuming.

In an attempt to reduce the amount of time needed to obtain a covering that is specifically shaped for the patient's head, some head-specific bandage solutions have been developed. For instance, U.S. Pat. No. 5,031,609 describes a postoperative compression bandage for the head which is formed of two identical flat portions affixed to one another forming a flat body, wherein the body can be wrapped around the patient's head and be secured in place by hook-and-loop fasteners comprised on certain edges of the flat portions. U.S. Patent Application No. 2009/0299259A1 describes a head trauma cap bandage and method which, when applied, applies compression pressure to stop bleeding; the head trauma bandage is cap-shaped and secured to the patient's head by a strap that wraps around the patient's mandible. U.S. Pat. No. 7,887,501 teaches a compressive head dressing comprising an elastomeric layer and a cinch for adjusting to the patient's head.

However, known solutions mainly focus on providing a head-shaped dressing and do not specifically address other problems such as being able to rapidly and efficiently provide treatment of head wounds.

Accordingly, there remains a need in the art to provide an adequate dressing cover for the head, a limb or a stump or an extremity of the human or animal body, which is optimized for such body part, facilitates treatment of wounds and is yet provided at reasonable cost.

SUMMARY OF THE INVENTION

The present invention overcomes the deficiencies of the known art and the problems that remain unsolved by providing a medical bandage specifically designed for the head, a limb or a stump, producing a dressing covering that can be rapidly, intuitively, and universally applied in the event of an emergency or trauma. Unlike conventional dressings, the medical bandage disclosed herein can open for rapid easy fitting without further traumatizing a head with patient supine. In addition, the medical bandage disclosed herein is useful for treating ongoing wound care needs, to stabilize and hold drains, view wounds, medicate, and allow for a rapid and universal dressing change which is designed for use for both the head and a limb.

The medical bandage presents a three-dimensional cap-like shape having a convex outer surface and a concave inner surface configured to conform to the head, limb or stump. The medical bandage is formed by several layers of material, namely an internal layer made of a soft, skin compatible fabric, an external layer made of breathable material, and an intermediate absorbent layer or, alternatively or complementarily, an intermediate flexible bladder. Means of adjustment such as side hook-and-loop straps can be included in order to adjust the bandage to the head, limb or stump, and provide necessary compression to coagulate and maintain an intact dressing to cover the wound and promote healing. In some embodiments, the bandage can be partially or totally elastic to provide adjustment. In some embodiments, the medical bandage not only provides a ready-to-apply cover for a wound, but also includes active treating agents such as coagulant agents, antimicrobial agents, heating agents, cooling agents, or a combination thereof. The medical bandage in accordance with the invention may be used not only to cover wounds, but also for other purposes such as treating or preventing hair loss.

Introducing a first embodiment of the invention, the present invention consists of a medical bandage comprising a main body, presenting a concave inner surface, a convex outer surface and an inner cavity delimited by the concave inner surface for at least partially receiving a head, limb or stump. At least part of the main body comprises a skin-compatible first layer, a second layer and a non-permeable third layer. The first layer is arranged closer to the inner cavity than the third layer, and the second layer is arranged between the first layer and the third layer. The main body further includes at least one through port for accessing the inner cavity of the main body from outside the main body and through the first, second and third layers.

In a second aspect, the non-permeable third layer can be breathable.

In another aspect, the first layer can include at least one of a coagulant agent, an antimicrobial agent, a heating agent and a cooling agent.

In another aspect, the second layer can include an absorbent material, and the first layer can be permeable to the passing of fluid from the concave inner surface towards the second layer.

In yet another aspect, the second layer can include at least one of a coagulant agent, an antimicrobial agent, a heating agent and a cooling agent, and the first layer can be permeable for the passing of the at least one of a coagulant agent, an antimicrobial agent, a heating agent and a cooling agent through the first layer and towards the inner cavity of the main body.

In another aspect, the second layer can comprise a flexible bladder provided with an internal cavity for housing at least one of a solid, a fluid and a gas, and the main body can further include at least one bladder access port for accessing the inner cavity of the inner bladder from outside the main body.

In another aspect, the inner cavity of the inner bladder can contain a solid substance that is exothermically reactive to a liquid such as water.

In another aspect, the main body can further include at least one adjustment strap, configured to adjustably attach two different sections of the main body.

In another aspect, the adjustment strap can be fixedly attached to a first section of the main body and disconnectably attachable to a second section of the main body.

In another aspect, opposite ends of the adjustment strap can be disconnectably attachable to different sections of the main body.

In another aspect, the adjustment strap can be disconnectably attachable to the main body by a hook-and-loop connection.

In another aspect, the main body defines a rim delimiting an opening for inserting a head, limb or stump therethrough towards the inner cavity of the main body, and the at least one adjustment strap can be attachable along the rim and parallel to the rim.

In another aspect, the main body can be at least partially elastic to adjustably fit onto a head, limb or stump.

In another aspect, the second layer can comprise at least one space through which the first and third layers directly face one another.

In another aspect, the first and third layers can comprise a perforated opening facing the space of the second layer.

In another aspect, the first, second and/or third layers can comprise a plurality of partial portions arranged adjacently to each other forming a cap-shape.

In another aspect, at least two partial portions of the second layer can be separated by a gap, through which the first and third layers directly face one another.

In another aspect, the first layer and third layer can comprise at least one pair of perforated seams facing the gap.

Introducing another embodiment of the invention, the present invention consists of a bandage comprising a cap-shaped main body, presenting a concave inner surface, a convex outer surface and an inner cavity delimited by the concave inner surface for at least partially receiving a head, limb or stump. At least part of the main body comprises a skin-compatible first layer, a second layer and a non-permeable third layer. The second layer comprises a flexible bladder provided with an internal cavity for housing at least one of a solid, a fluid and a gas. The first layer is arranged closer to the inner cavity than the third layer, and the second layer is arranged between the first layer and the third layer. The main body further includes at least one bladder access port for accessing the inner cavity of the inner bladder from outside the main body. In addition, the main body includes at least one through port for accessing the inner cavity of the main body from outside the main body and through the first, second and third layers.

Introducing yet another embodiment of the invention, the present invention consists of a bandage comprising a cap-shaped main body, presenting a concave inner surface, a convex outer surface and an inner cavity delimited by the concave inner surface for at least partially receiving a head, limb or stump, the main body defining a rim delimiting an opening for inserting the head, limb or stump therethrough towards the inner cavity of the main body. At least part of the main body comprises a skin-compatible first layer, a second layer and a non-permeable third layer. The second layer includes a flexible bladder provided with an internal cavity for housing at least one of a solid, a fluid and a gas. The first layer is arranged closer to the inner cavity than the third layer, and the second layer is arranged between the first layer and the third layer. The main body further includes at least one bladder access port for accessing the inner cavity of the inner bladder from outside the main body. In addition, the main body includes at least one through port for accessing the inner cavity of the main body from outside the main body and through the first, second and third layers. At least one adjustment strap is configured to adjustably extend along the rim and between two different sections of the main body.

These and other advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

In this document, relational terms such as "first" and "second," "top" and "bottom," and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a . . . " does not, without more constraints, preclude the existence of additional identical elements in the process, method, article, or apparatus that comprises the element.

Figure 1:
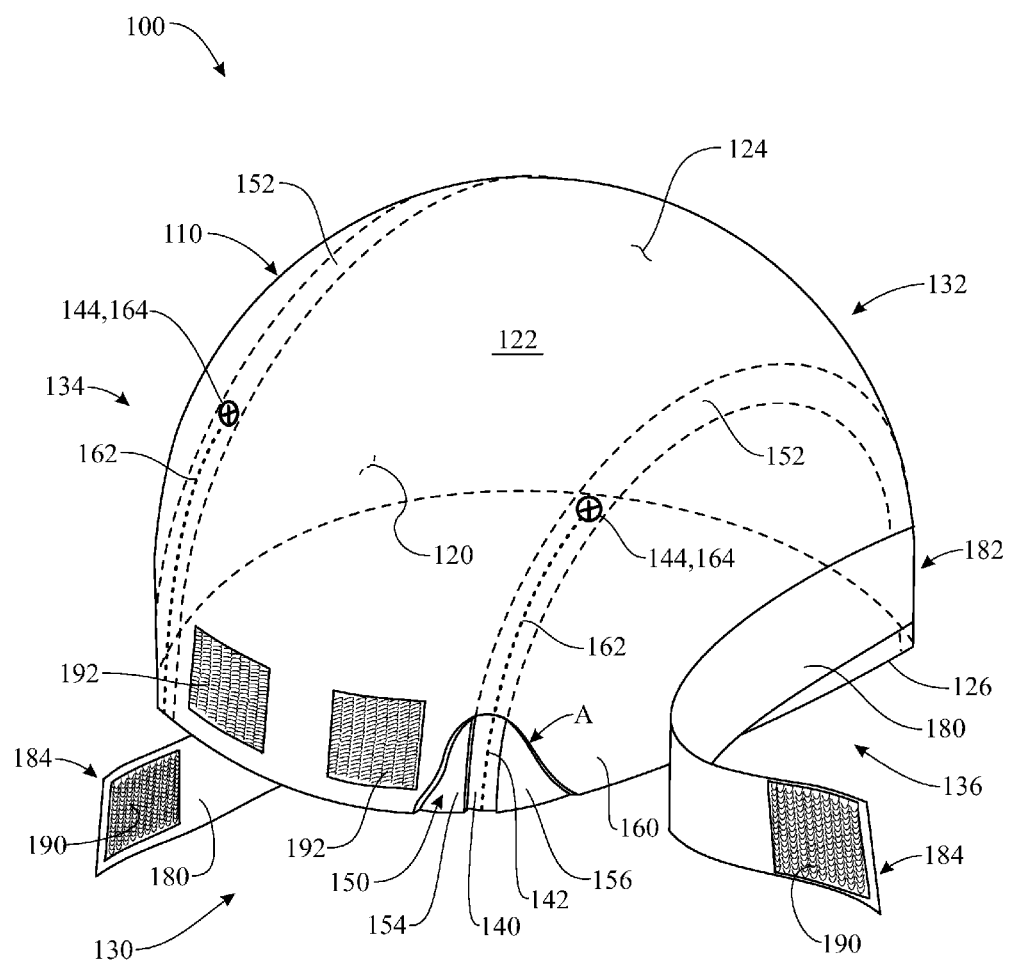
FIG. 1 presents a detailed perspective view of a first exemplary medical bandage in accordance with the invention, the view including an exemplary cut-out portion for unveiling the otherwise concealed first and second layers.

The illustration of FIG. 1 presents a first exemplary embodiment of a medical bandage 100 in accordance with the invention. The medical bandage 100 comprises a main body 110 that is in shape of a cap. The main body 110 presents a concave, inner surface 120 delimiting a head-, limb- or stump-receiving cavity 122, and a convex, outer surface 124, where the inner and outer surfaces 120, 124 converge in a perimetric rim 126. The main body 110 further presents a front side 130, a rear side 132, a right side 134 and a left side 136.

Figure 6:
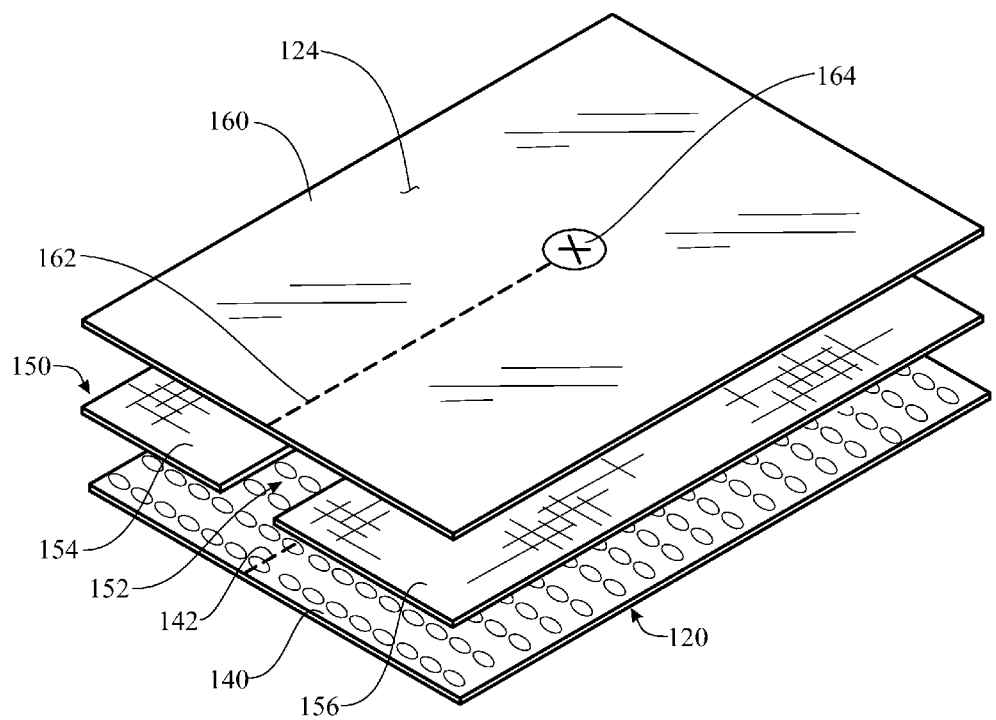
FIG. 6 presents an enlarged perspective view of the layers comprised in the medical bandage of FIG. 1.

Several layers and materials form the main body 110, namely a skin-compatible first layer 140, an absorbent second layer 150, and a breathable, non-permeable third layer 160, as shown in the general perspective view of FIG. 1 and in the enlarged, exploded view of FIG. 6. The first layer 140 and second layer 150 can be manufactured, for instance, from cloth, gauze, cotton, polyurethane, or a combination thereof. The third layer 160 can be manufactured, for instance, as a polyethylene film. For better understanding of the layered arrangement, an illustrative cut-out A has been carried out in the third layer 160 of FIG. 1, unveiling the inner first and second layers 140, 150. As shown, the first layer 140 is arranged closer to the inner surface 120; in the present embodiment, in particular, the first layer 140 is in fact the innermost layer, and thus the innermost surface of the first layer 140 provides the main body inner surface 120. In turn, the third layer 160 is arranged closer to the outer surface 124; in the present embodiment, in particular, the third layer 160 is in fact the outermost layer, and the outermost surface of the third layer 160 provides the main body outer surface 124. The second layer 150 is arranged between the first layer 140 and the third layer 160; the second layer 150 of the present embodiment is, in fact, arranged immediately between the first layer 140 and the third layer 160. Thus, the main body in accordance with the invention can comprise three or more layers, the main body 110 of the present embodiment specifically consisting of three layers 140, 150, 160. In addition, the first layer 140 is permeable to the passing of fluid from the inner surface 120 towards the absorbent second layer 150, while the non-permeable third layer 160 keeps liquids and optionally gasses within the absorbent second layer 150. All layers 140, 150, 160 can have a variable thickness. The first and second layers 140, 150 can have a variable permeability and absorbency. The second layer 150, in particular, can be manufactured having different thicknesses in order to provide a variable degree absorbency and cushioned feel and wound-healing properties.

As shown in FIG. 1, the medical bandage 100 can further include one or more adjustment straps 180, each configured to adjustably attach to two different sections or zones of the main body 110, and provide compression if needed. The one or more straps can be arranged in a variety of directions. In the present embodiment, for instance, the medical bandage 100 includes two straps 180, wherein each strap 180 is arranged from the main body rear side 132 to the main body front side 130, extending along the right side 134 and left side 136, respectively. Being able to adjust the level of tightness with which the two straps 180 are attached allows adjusting the size of the cap-shaped main body 110 to different head, limb or stump sizes, and applying needed pressure or coverage to help stop bleeding, keep the bandage secure, and protect the wound, thereby promoting wound healing and assisting in post trauma/surgical care.

In the present embodiment, a first end 182 of the adjustment straps 180 is fixedly attached to the main body rear side 132 and an opposite second end 184 is disconnectably attachable to the main body front side 130. Thus, the straps 180 are permanently attached to the main body 110, preventing the straps 180 from being inadvertently lost when their second end 184 is detached from the main body 110, and yet are easily and rapidly detachable to readjust the fitting of the cap on a head or limb.

In the present embodiment, the straps 180 are disconnectably attachable to the main body 110 by a hook-and-loop connection formed by a first hook-and-loop element 190 forming part of the strap 180 and a compatible second hook-and-loop element 192 included in the main body 110. A hook-and-loop connection is advantageous in that it is easy and rapidly connected and disconnected, provides a secure and resistant attachment, and is a cost effective solution. In addition, it can be easily and rapidly tightened in the event that a greater pressure (or even a tourniquet effect) is required on the wound; similarly, the hook-and-loop connection can be easily and rapidly loosened in the event that an excessive pressure is being applied that is causing discomfort in the patient.

Furthermore, the straps 180 of the present embodiment are arranged to extend along the right side 134 and left side 136, respectively, generally along the rim 126 and parallel to the rim 126. Thus, when the straps 180 are relatively tightly fastened to provide a snug fitting of the cap onto the patient's head or limb, the straps 180 provide a uniform pressure along a substantial length of the rim 126. In consequence, the adjusted bandage 100 is very safely secured and yet does not cause discomfort to the patient.

Alternative embodiments of the invention can comprise a different number of straps. In addition, one or more straps can have both opposite ends disconnectably attachable to different sections of the main body, instead of having one end permanently affixed to the main body. In further embodiments, the main body can be at least partially elastic to adjustably fit onto a head, a limb or a stump. For instance, the first and/or third layers 140, 160 could be provided with an elastic band along the cap-shaped main body rim 126 so that the area of the rim 126 tightly (but comfortably) adjusts to the head, limb or stump while the rest of the main body 110 is more loosely fitted. In another example, the entire first layer 140 and/or third layer 160 can be elastic, to provide a compressive effect on the head, limb or stump that can be convenient for stopping wound bleeding or other applicable medical needs. In general, it is contemplated that the bandage 100 can be configured to snugly fit onto the head, limb or stump, in order for the first layer 140 to contact the wound, or to be more loosely arranged so that the first layer 140 does not contact the wound.

The bandage in accordance with the invention includes at least one port providing selective access to the cavity from outside the bandage. A nurse or other medical processional can thus easily insert a needle, tube or other medical device through the port, without having to reposition or remove the bandage from the patient's head or limb. A tube can be supported by a port, or repositioned from one port to another, without requiring the use of tape. For example, the present embodiment provides two elongated through ports 112 and two punctual or discrete through ports 114. The discrete through ports 114 allow for a rapid and adjusted insertion of the syringe or tube at specific, predetermined spots. The elongated through ports 112, instead, allow the medical professional to select where along the elongated port 112 to insert the syringe or tube, permitting a more versatile and personalized treatment.

The elongated through ports 112 of the present embodiment are constructed by having the first and third layers 140, 160 include two respective scored or perforated elongated seams 142, 162 arranged aligned or in registration and that can be quickly and rapidly torn or opened in order to apply a medicine onto, disinfect or treat a wound, or visually inspect the wound; the second layer 150 can comprise a similar scored or perforated seam in registration with the elongated seams 142, 162 of the first and third layers 140, 160 or, alternatively, as shown in FIG. 1, the second layer 150 can include two respective elongated channels or spaces 152 through which the first and third layers 140, 160, and more particularly elongated seams 142, 162, face each other directly.

In turn, the discrete through ports 114 are formed by two respective aligned perforated openings 144, 164 located at the end of the perforated seams 142, 162 of the first and third layers 140, 160 and in registration with the corresponding space 152 of the second layer 150. One or both openings 144, 164 can be scored or perforated X-cut openings, as shown, or present any other applicable shape such as an O-shape. In addition, alternative embodiments are contemplated such as having aligned openings on all three layers 140, 150, 160. It is also contemplated that an opening on the outer, third layer 160 can be initially closed or sealed and only accessible therethrough when ripped or perforated, while an opening on the first and/or second layer 140, 150 can be initially open and readily accessible once the opening on the third layer 160 is ripped or perforated.

Figure 2:
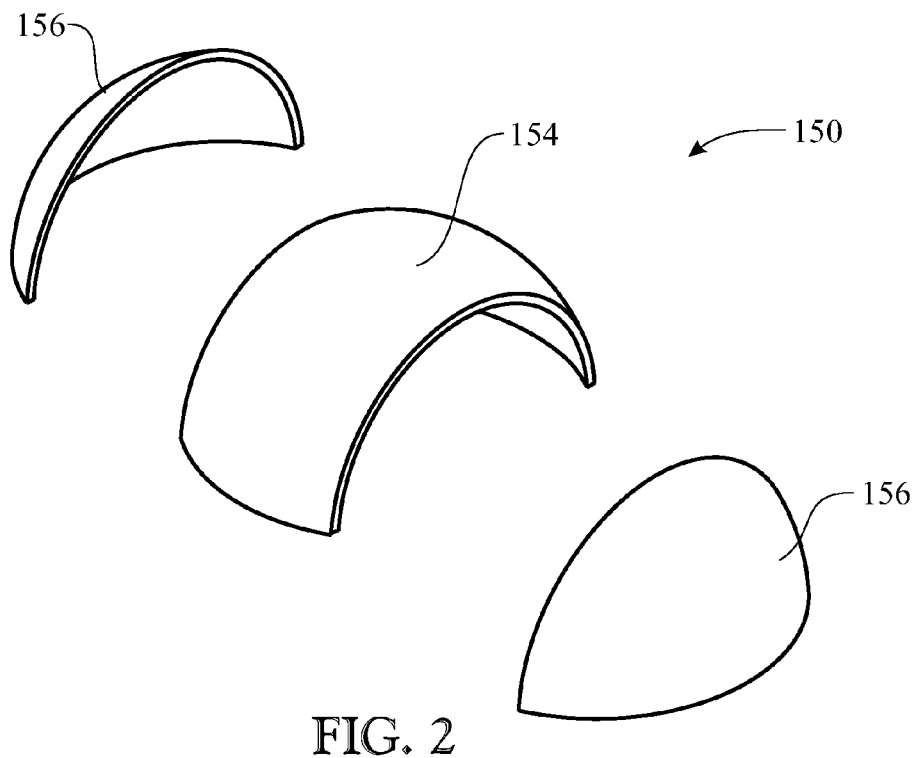
FIG. 2 presents an exploded view of the second layer, showing the partial portions forming the layer.
Figure 3:
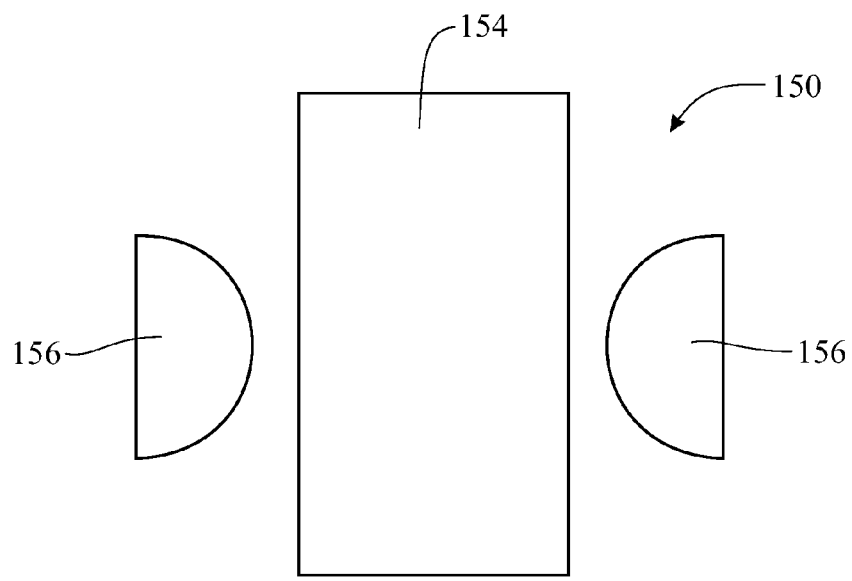
FIG. 3 presents a top plan view of the partial portions of FIG. 2.

Preferably, any one of the first layer 140, the second layer 150 and the third layer 160 can be formed of a plurality of partial portions, arranged adjacent to one another in order for the layer to adopt a three-dimensional cap shape. For instance, as best shown in FIGS. 2 and 3, the second layer 150 of the present embodiment is formed by one longitudinal partial portion 154, which is configured to extend form a frontal area to an occipital area, and two separate opposite side partial portions 156. Such a construction is cost effective as it utilizes a minimum amount of flat-shaped partial portions (as best shown in FIG. 3) to build a three-dimensional cap-shaped second layer 150. The longitudinal partial portion 154 is rectangular, and the opposite side partial portions 156 are semicircular, all of which being simple shapes that may be manufactured at reasonable cost.

As can be observed in FIG. 1, the present embodiment is such that the elongated spaces 152 of the second layer 150 are carried out as respective gaps that have been left between adjacent partial portions 154, 156. Thus, perforation of the second layer partial portions 154, 156 manufacturing the product is avoided, and the cost of manufacture is kept reasonable. The three partial portions 154, 156 of the second layer 150 are kept in place by the first and third layers 140, 160. Optionally, an adhesive, stitching, scoring or the like can be applied to further maintain the relative position of the three layers 140, 150, 160. Any seams can be constructed so that they can be relatively easily torn, allowing for easy dressing changes.

The absorbent, second layer 150 can further include at least one coagulant agent, such as clay-based coagulants (kaolin, chitosan, talc), synthetic coagulants (e.g., polymers), animal-based coagulants (e.g., gelatins), plant-based coagulants (e.g., cellulose) or a combination thereof, preferably embedded in the absorbent layer material or applied on the absorbent layer material. In such an event, the first layer 140 is configured to be permeable for the outward passing of the coagulant agent towards the main body inner surface 120 and the cavity 122. In alternative embodiments, at least one coagulant agent can be included in the first layer 140, in closer proximity to the wound.

In addition, the absorbent second layer 150 can include at least one antimicrobial agent, such as zincs or silvers, in order to prevent bacterial, fungal or parasite infection of the wound. The antimicrobial agent is preferably embedded in the absorbent layer material or applied on the absorbent layer material. The first layer 140 is then permeable for the outward passing of the antimicrobial agent towards the main body inner surface 120 and the cavity 122. In alternative embodiments, at least one antimicrobial agent can be included in the first layer 140, in closer proximity to the wound.

The absorbent second layer 150 can also include at least one heating (exothermic) agent and/or at least one cooling (endothermic) agent, such as a metal oxide, ureas, citric acid, bicarbonates or a combination thereof, in order to prevent heat loss from the head, limb or stump. The heating agent and/or cooling agent is preferably embedded in the absorbent layer material or applied on the absorbent layer material. The first layer 140 is permeable for the passing of the at least one heating agent and/or cooling agent through the first layer 140 and towards the main body concave, inner surface 120 and the cavity 122. In alternative embodiments, at least one heating agent and/or cooling agent can be included in the first layer 140, in closer proximity to the wound.

In some embodiments, the medical bandage is packaged clean and sterile and intended for single use only, whereas in other embodiments the medical bandage is a multi-use, washable bandage which can be subjected to cleaning and sterilization.

In summary, the invention provides a cap-shaped bandage capable of being fitted on a head, a limb or a stump, and even onto a toe, a finger, a sexual organ or other appendage of the human or animal body, comprising an inner skin-compatible layer capable of allowing body fluids from the wound to pass through, an intermediate absorbent layer capable of absorbing the body fluids, and an external breathable non-permeable layer for concealing the absorbent layer, retaining fluids within the absorbent layer and providing a clean finish to the bandage. In addition, the cap-shaped bandage includes at least one port for accessing the bandage inner cavity from the outside. The medical bandage 100 may be efficacious for a variety of therapeutic functions, including, without limitation, stemming the flow of body fluids, absorbing body fluids, easing pain, debriding the wound, protecting from infection, promoting healing, and reducing psychological stress.

Figure 4:
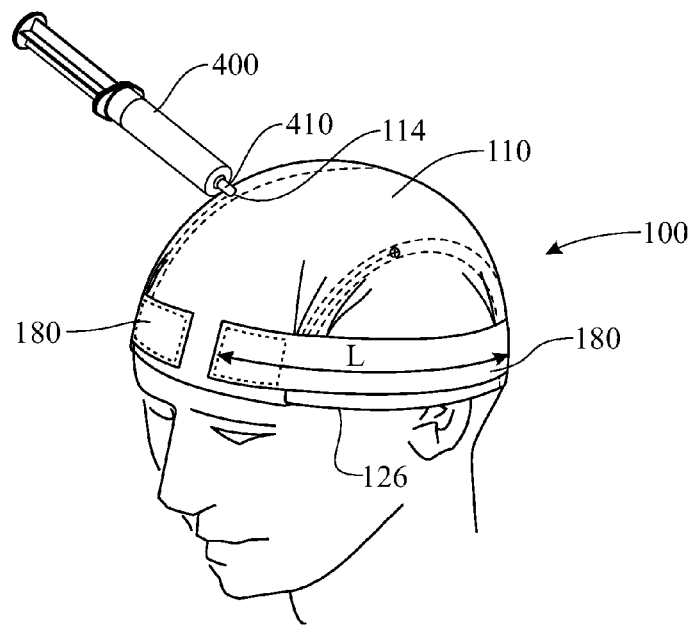
FIG. 4 presents a perspective view of the exemplary medical bandage of FIG. 1 fitted onto a person's head, and a syringe being applied onto a discrete port of the bandage in order to inject a medicine into the internal cavity of the bandage.

For instance, the illustration of FIG. 4 shows the bandage 100 applied on a patient's head, wherein the straps 180 have been tensioned and fastened to provide a lateral adjustment of the main body 110 against the periphery of the head, over the ears. As shown, the straps 180 extend along either side of the head in a generally symmetrical fashion, along and parallel to the rim 126, providing a snug adjustment of the cap. Since the straps 180 achieve a uniform pressure along a respective substantial length L, the straps 180 create no pressure points and cause no added discomfort to the patient. In addition, a syringe 400 has been inserted through one of the discrete through ports 114 by passing the syringe tip 410 through the opening 164 of the third layer 160, the corresponding elongated space 152 of the second layer 150 and the corresponding opening 144 of the first layer 140. Operation of the syringe causes a medicine contained in the syringe to be delivered directly into the cavity 122 and onto a wound without having to move the bandage 100 to a different position on the patient's head or without having to partially or completely remove the bandage 100 from the patient's head.

Figure 5:
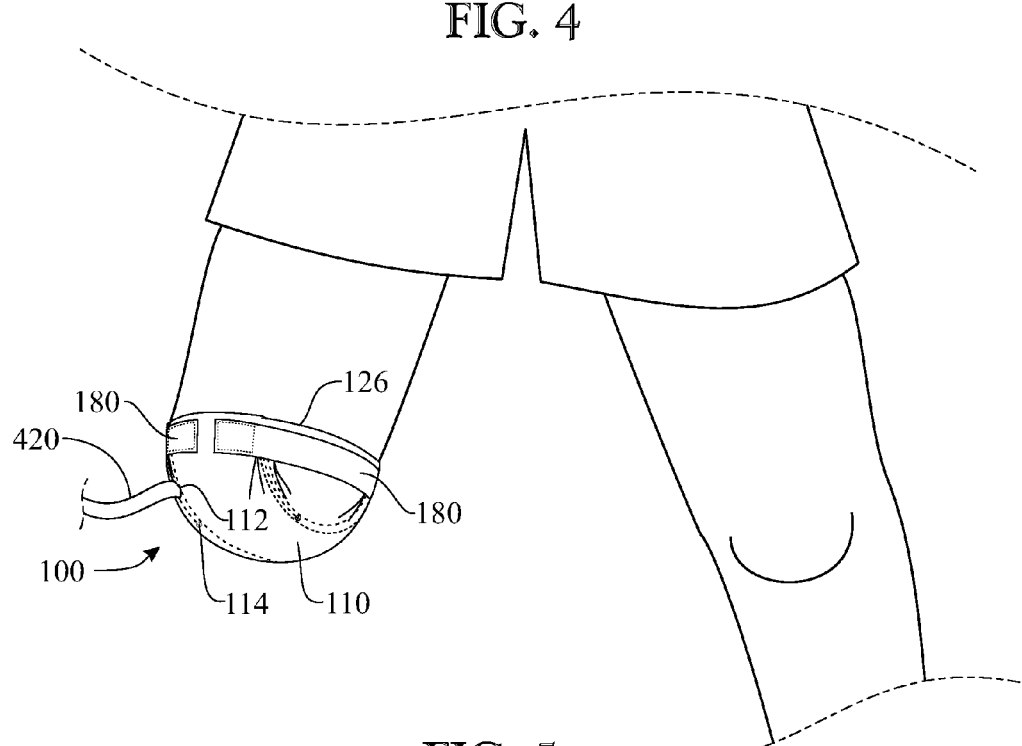
FIG. 5 presents a perspective view of the exemplary medical bandage of FIG. 1 fitted onto an amputated limb, having inserted a drainage tube through an elongated through port formed by partially opening aligned perforated seams providing selective access to the bandage internal cavity.

The illustration of FIG. 5 shows the bandage 100 placed covering a stump, where placement is again carried out by correctly positioning the cap-shaped main body 110, and tightening and attaching the straps 180 along and parallel to the rim 126. The medical professional has further inserted a drainage tube 420 through an elongated through port 112, which has been previously formed by tearing a length of the perforated seams 142, 162 of the first and third layers 140, 160 in order to open a passageway through the opened seams 142, 162 and the elongated space 152. Direct access to a wound in order to remove body fluids from the wound is therefore achieved without having to re-position or remove the bandage 100, thus preventing further discomfort to the patient.

Therefore, a single device is provided that can be intuitively and universally used to cover either a wound on the head or a wound on a stump. In addition, the device is extremely easy and convenient to use, saving precious medical treatment time and allowing a more rapid care of severe wounds, and ongoing treatment of chronic wounds. Being able to dress a wound more rapidly is greatly beneficial for the patient, as bleeding can be controlled much sooner by means of the immediate stop effect provided by the direct placement of the bandage; in addition, the wound exposure time is cut down, thereby reducing the risk of infection.

Figure 7:
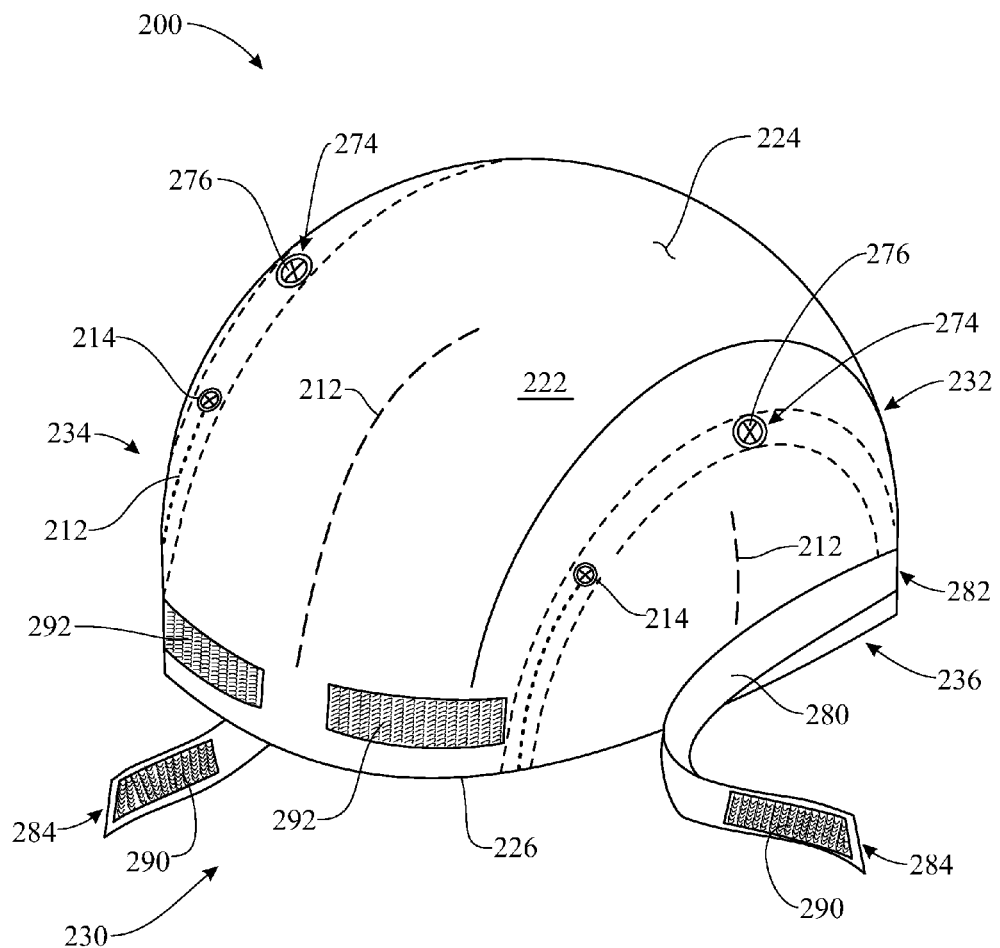
FIG. 7 presents a detailed perspective view of a second exemplary medical bandage in accordance with the invention.

The illustrations of FIGS. 7 through 10 present a bandage 200 in accordance with a second exemplary embodiment of the invention. Like features of the bandage 200 of FIGS. 7 through 10 and the bandage 100 of FIGS. 1 through 6 are numbered the same except preceded by the numeral '2'. As in the previous embodiment, the bandage 200 comprises a main body 210 having a front side 230, a rear side 232, a right side 234a left side 236, an inner surface 220, an outer surface 224, an internal cavity 222 for receiving a head or stump, and a bottom edge or rim 226 delimiting a bottom opening for inserting the head or stump into the cavity 222. The main body 210 further includes several elongated through ports 212 and two punctual or discrete through ports 214 providing access to the internal cavity 222 from outside the bandage 200. Two straps 180 extend from the rear side 232 to the front side 230 of the main body 210, along the left and right sides 236, 234, respectively, and along the rim 226 and parallel to the rim 226. Similarly to the previous embodiment, a first end 282 of the adjustment straps 280 is fixedly attached to the main body rear side 232 and an opposite second end 284 is disconnectably attachable to the main body front side 230. The straps 280 are disconnectably attachable to the main body 210 by a hook-and-loop connection formed by a first hook-and-loop element 290 forming part of the strap 280 and a compatible second hook-and-loop element 292 included in the main body 210. As shown in FIG. 7, the first and second hook-and-loop elements 290, 292 are elongated and arranged parallel to the rim 226, thereby increasing the adjustment range provided by the straps 280 and thus favoring that a single-size bandage 200 is usable on different head sizes or body parts.

The main body 210 is formed of an innermost soft, skin-compatible first layer 240, an outermost non-permeable third layer 260, and an intermediate second layer. The second layer of the present embodiment is a flexible bladder 270, i.e. a flexible non-permeable layer comprising an internal cavity 272 for housing at least one solid substance, at least one liquid substance, at least one gaseous substance, or combinations thereof. A bladder access port 274 provides access to the internal cavity 272, for instance in order to inject air or warm water into the internal cavity 272. The bladder access port 274 of the present embodiment is initially closed by a perforable or tearable membrane 276, which can optionally include an X-shaped score or other predefined score to facilitate tearing or perforating the membrane 276 with a syringe or manually, to name a few examples. In some embodiments, the internal cavity 272 can be provided with isolated or non-isolated compartments to promote a uniform distribution of the substance(s) within the cavity.

Figure 8:
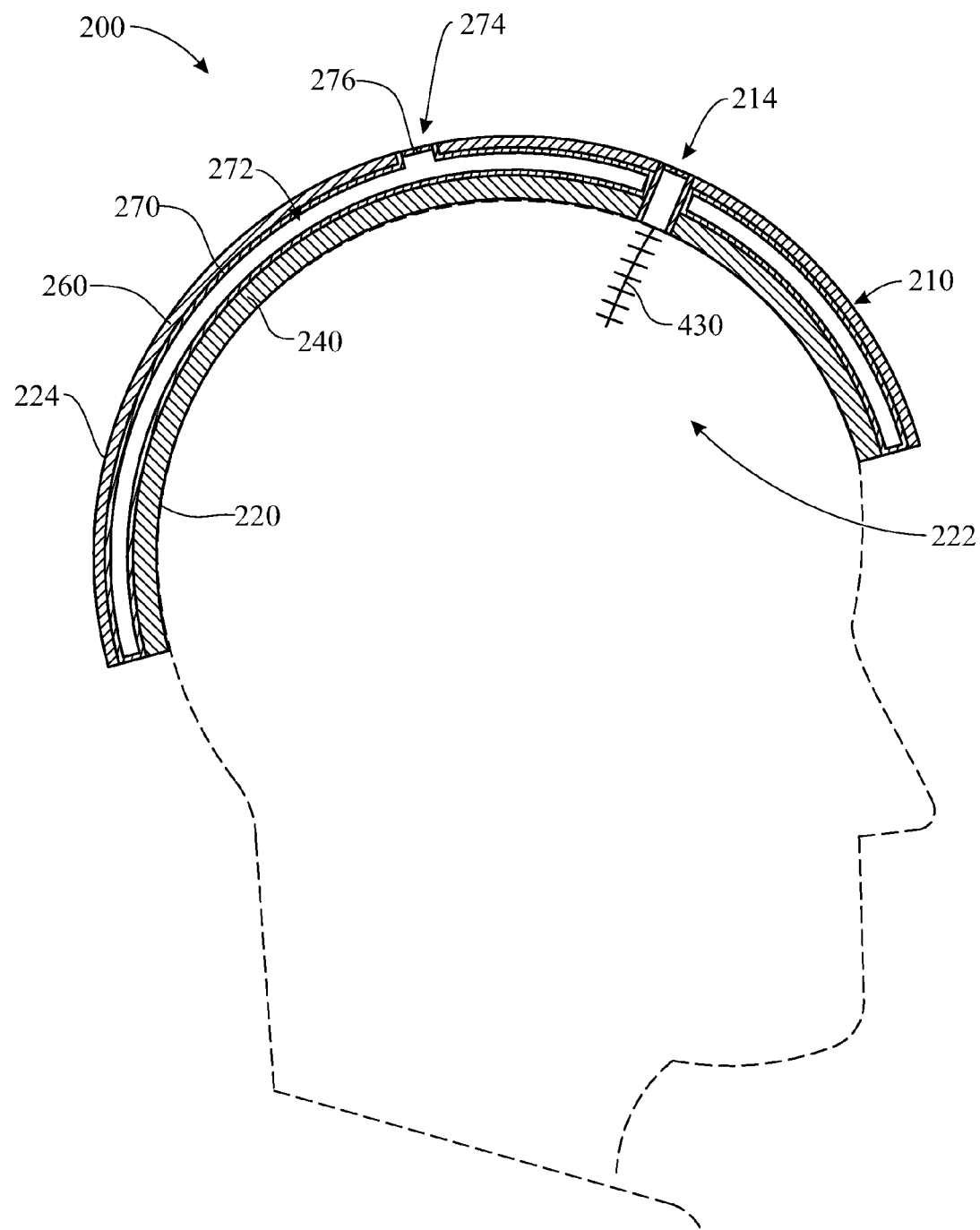
FIG. 8 presents a cross-sectional side elevation view of the medical bandage of FIG. 7 fitted onto a patient's head, in accordance with a first application in which the bandage is simply applied onto and adjusted to the head.
Figure 9:
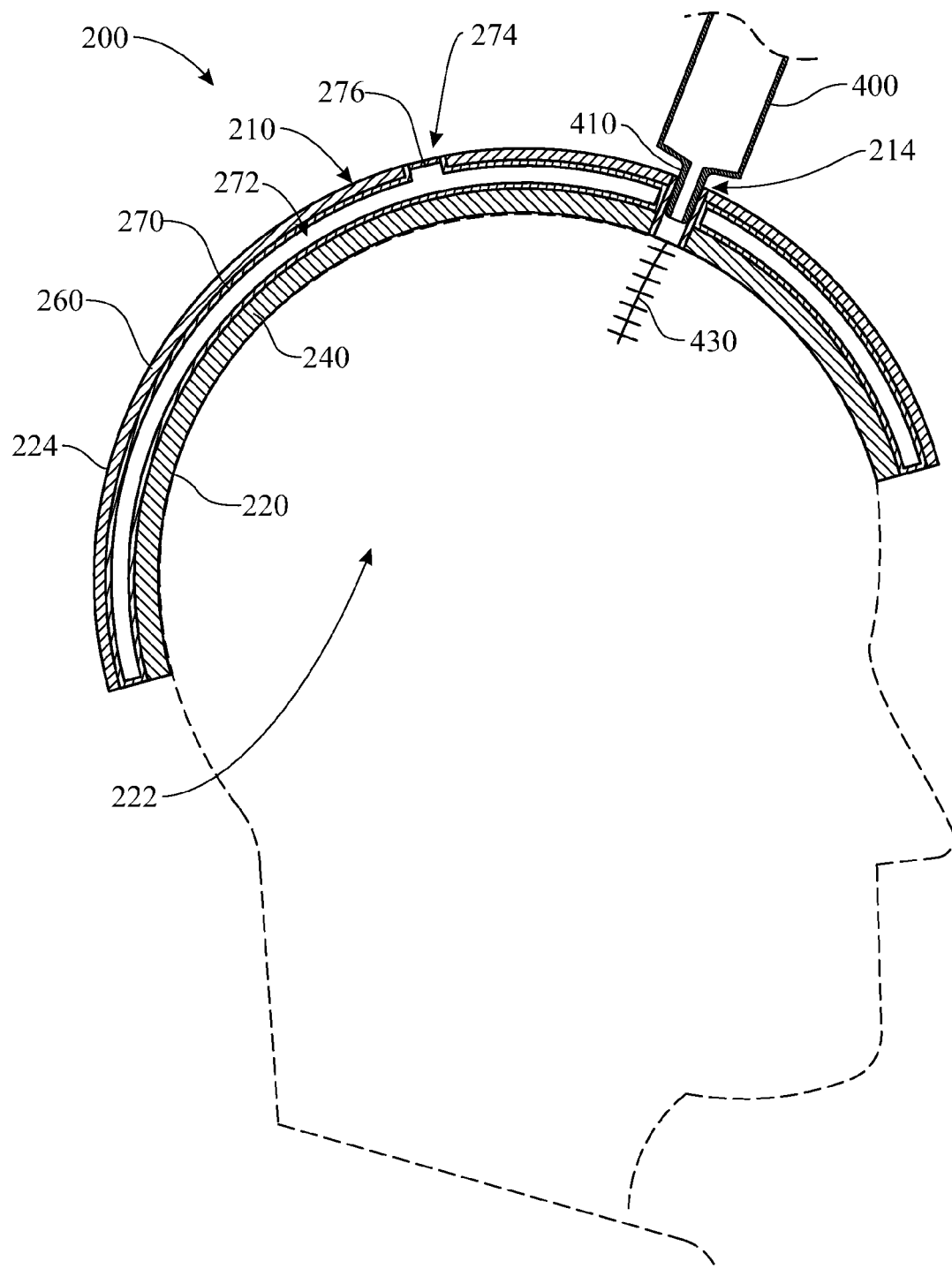
FIG. 9 presents a cross-sectional side elevation view of the medical bandage of FIG. 7 fitted onto a patient's head, in accordance with a second application, in which a syringe is inserted into a discrete through port in order to deliver a medicine to a wound on the head.
Figure 10:
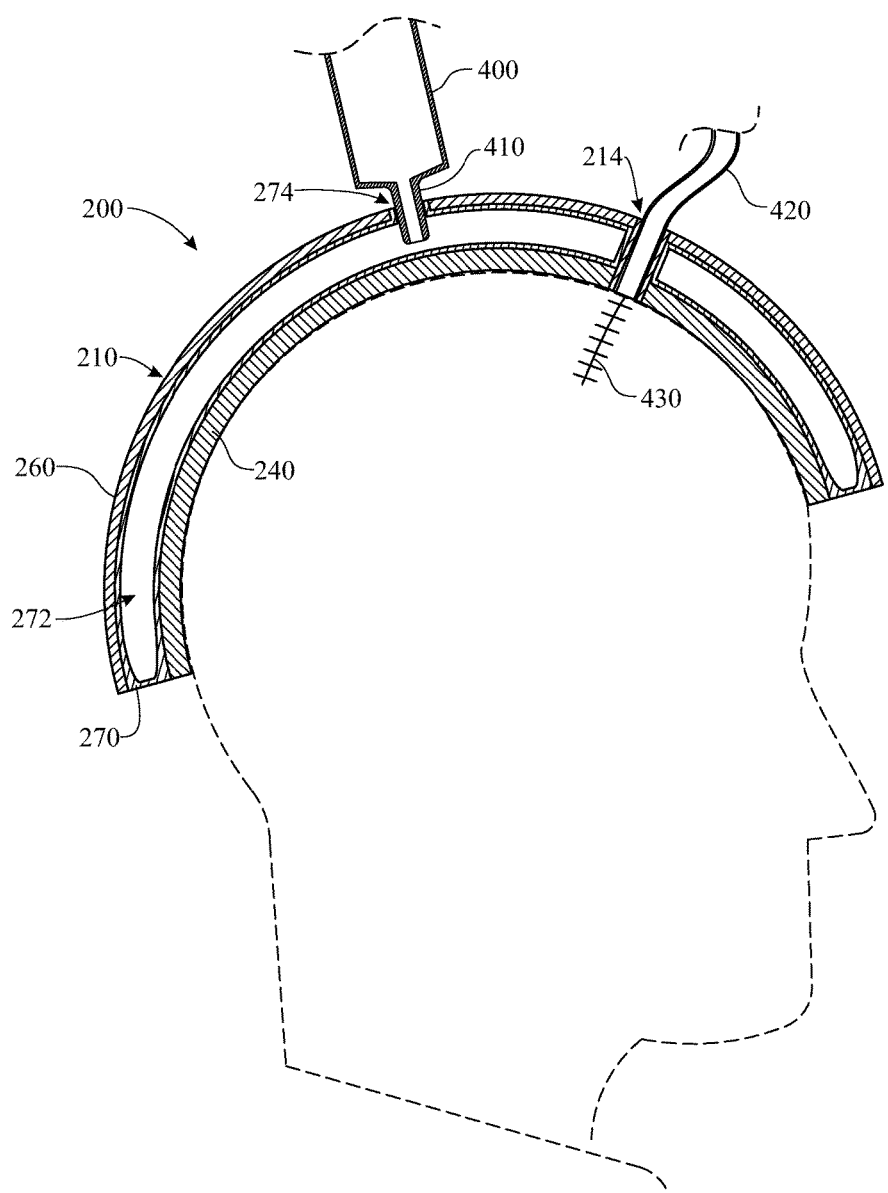
FIG. 10 presents a cross-sectional side elevation view of the medical bandage of FIG. 7 fitted onto a patient's head, in accordance with a third application, in which a syringe is inserted into a bladder access port to inject air or a liquid or solid medicament, and inflate the bandage to provide light compression to a wound, and a drainage tube is inserted into a discrete through port in order to remove body fluids from the wound.

The illustrations of FIGS. 8 through 10 depict several usage scenarios of the bandage of FIG. 7. Referring initially to FIG. 8, the bandage 200 is shown fitted onto a patient's head in order to provide an adjusted dressing of the head in the event of a trauma or wounds. The illustration of FIG. 9, in turn, shows the bandage 200 fitted onto a patient's head and a syringe 400 having perforated and penetrated a discrete through port 214 and in the process of administering a liquid medicine onto a wound 430. Finally, the illustration of FIG. 10 presents a further application in which the bandage 200 has been fitted onto a patient's head and a nozzle or syringe 400 has perforated and penetrated the bladder access port 274 and has injected air into the inner flexible bladder 270, causing the flexible bladder 270 to expand and the bandage 200 to compress the head of the patient, such as to stop bleeding of a wound 430. In turn, a drainage tube 420 has been inserted through a discrete through port 214 in order to remove body fluids from a wound 430. In a further application, not shown in the drawings, a vacuum tube could be inserted into a discrete through port 214 and a suction force could be applied through the vacuum tube in order to create a vacuum inside the bandage 200, thereby removing air from the internal cavity of the main body and thus reducing the risk of contamination of the wound as well as increasing compression of the wound.

In some embodiments, the internal cavity 272 of the flexible bladder 270 can hold solid substances for specific treatment purposes. For instance and without limitation, the bandage 200 can be manufactured in such a way that the internal cavity 272 is marketed containing solid substances that are configured to exothermically react with a liquid (e.g., water). Thus, when placing the bandage 200 on the patient's head or limb, the medical professional can inject water through the bladder access port 274 to cause an exothermic reaction between the water and the solid substances and thus warm the bandage 200.

Alternative embodiments are contemplated in which the main body includes both an internal flexible bladder and an internal absorbent layer, in which case the flexible bladder is preferably arranged externally to the absorbent layer. The main body is therefore capable of absorbing and retaining body fluids from a wound and simultaneously compressing the wound, for instance to stop the wound from bleeding.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims, including any amendments made during the pendency of this application, and all equivalents of those claims as issued.

What is claimed is:

1. A medical bandage comprising:
   a main body, presenting a concave inner surface, a convex outer surface and an inner cavity delimited by the concave inner surface for at least partially receiving a head, limb or stump, wherein at least part of said main body comprises:
   a skin-compatible first layer;
   a second layer;
   a non-permeable third layer, wherein
   the first layer is arranged closer to the inner cavity than the third layer, and further wherein
   the second layer is arranged between the first layer and the third layer and comprises at least one space through which the first and third layers directly face one another; and
   at least one through port for accessing the inner cavity of the main body from outside the main body and through the first, second and third layers, or for stabilizing or supporting a drain or tubing passing through the port.

2. The medical bandage of claim 1, wherein said at least one through port is provided by scored lines and can adopt a closed position in which the scored lines are not torn, and an open position in which the scored lines are torn open providing quick access to the inner cavity.

3. The medical bandage of claim 1, wherein the first layer includes at least one of a coagulant agent, an antimicrobial agent, a heating agent and a cooling agent.

4. The medical bandage of claim 1, wherein the second layer comprises an absorbent material, and the first layer is permeable to the passing of fluid from the concave inner surface towards the second layer.

5. The medical bandage of claim 4, wherein the second layer includes at least one of a coagulant agent, an antimicrobial agent, a heating agent and a cooling agent, and the first layer is permeable for the passing of said at least one of a coagulant agent, an antimicrobial agent, a heating agent and a cooling agent through the first layer and towards the inner cavity of the main body.

6. The medical bandage of claim 1, wherein said second layer comprises a flexible bladder provided with an internal cavity for housing at least one of a solid, a fluid and a gas, said main body further comprising at least one bladder access port for accessing the inner cavity of the inner bladder from outside the main body.

7. The medical bandage of claim 6, wherein said inner cavity of said inner bladder contains a solid substance that is exothermically reactive to a liquid.

8. The medical bandage of claim 1, wherein the main body further comprises at least one adjustment strap, configured to adjustably attach two different sections of the main body.

9. The medical bandage of claim 8, wherein the adjustment strap is fixedly attached to a first section of the main body and disconnectably attachable to a second section of the main body.

10. The medical bandage of claim 8, wherein opposite ends of the adjustment strap are disconnectably attachable to different sections of the main body.

11. The medical bandage of claim 8, wherein the adjustment strap is disconnectably attachable to the main body by a hook-and-loop connection.

12. The medical bandage of claim 8, wherein said main body defines a rim delimiting an opening for inserting a head, limb or stump therethrough towards the inner cavity of the main body, wherein said at least one adjustment strap is attachable along said rim and parallel to said rim.

13. The medical bandage of claim 1, wherein the main body is at least partially elastic to adjustably fit onto a head, limb or stump.

14. The medical bandage of claim 1, wherein the first and third layers comprise a perforated opening facing the space of the second layer.

15. The medical bandage of claim 1, wherein the first, second and/or third layers comprise a plurality of partial portions, which are arranged adjacently to each other forming a cap-shape.

16. The medical bandage of claim 15, wherein at least two partial portions of the second layer are separated by a gap, through which the first and third layers directly face one another.

17. The medical bandage of claim 16, wherein the first layer and third layer comprise at least one pair of perforated seams facing the gap.

18. A medical bandage comprising:
a main body, presenting a concave inner surface, a convex outer surface and an inner cavity delimited by the concave inner surface for at least partially receiving a head, limb or stump, wherein at least part of said main body comprises:
a skin-compatible first layer;
a second layer;
a non-permeable third layer, wherein
the first layer is arranged closer to the inner cavity than the third layer, and the second layer is arranged between the first layer and the third layer; and
at least one through port for accessing the inner cavity of the main body from outside the main body and through the first, second and third layers, or for stabilizing or supporting a drain or tubing passing through the port; wherein
the first, second and/or third layers comprise a plurality of partial portions, which are arranged adjacently to each other forming a cap-shape; and further wherein
at least two partial portions of the second layer are separated by a gap, through which the first and third layers directly face one another.

19. A medical bandage comprising:
a main body, presenting a concave inner surface, a convex outer surface and an inner cavity delimited by the concave inner surface for at least partially receiving a head, limb or stump, wherein at least part of said main body comprises:
a skin-compatible first layer;
a second layer;
a non-permeable third layer, wherein
the first layer is arranged closer to the inner cavity than the third layer, and the second layer is arranged between the first layer and the third layer; and
at least one through port for accessing the inner cavity of the main body from outside the main body and through the first, second and third layers, or for stabilizing or supporting a drain or tubing passing through the port; wherein
the first, second and/or third layers comprise a plurality of partial portions, which are arranged adjacently to each other forming a cap-shape; and further wherein
at least two partial portions of the second layer are separated by a gap, through which the first and third layers directly face one another, and the first layer and third layer comprise at least one pair of perforated seams facing the gap.

\* \* \* \* \*